United States Patent [19]

Carter

[11] Patent Number: 4,798,604

[45] Date of Patent: Jan. 17, 1989

[54] CONTOURED FILM

[75] Inventor: Andrew J. Carter, Saffron Walden, United Kingdom

[73] Assignee: Smith and Nephew Associated Companies p.l.c., United Kingdom

[21] Appl. No.: 52,855

[22] PCT Filed: Aug. 26, 1986

[86] PCT No.: PCT/GB86/00504

§ 371 Date: Apr. 15, 1987

§ 102(e) Date: Apr. 15, 1987

[87] PCT Pub. No.: WO87/01029

PCT Pub. Date: Feb. 26, 1987

[30] Foreign Application Priority Data

Aug. 24, 1985 [GB] United Kingdom ............. 8521254

[51] Int. Cl.⁴ .............................. A61F 13/16
[52] U.S. Cl. ............................ 604/383; 604/366; 604/370
[58] Field of Search ............ 604/366, 369, 370, 382, 604/383

[56] References Cited

U.S. PATENT DOCUMENTS 3,292,619 12/1966 Egler .
4,055,180 10/1977 Karami ........................... 604/366

FOREIGN PATENT DOCUMENTS 0117351 10/1984 European Pat. Off. .
171268   2/1986 European Pat. Off. .
1526778  9/1978 United Kingdom .

Primary Examiner—John D. Yasko
Attorney, Agent, or Firm—Jacobs & Jacobs

[57] ABSTRACT

A water permeable, contoured, polymeric film which is apertured and which contains a pattern of raised areas. The film is formed from elastomeric polymer, preferably a blend of ethylene-vinyl acetate copolymer with incompatible polymer. The numbers of apertures and raised areas contained in the film are such that the ratio of apertures to raised areas is greater than unity. The apertures are preferably distributed in a random manner throughout the raised areas. Processes for forming the film by first aperturing the film and then impressing raised areas into the apertured film are also described. The film may be employed to form the body contacting surface in absorbent devices. The use of the film helps to reduce the phenomenon of wet-back.

29 Claims, No Drawings

CONTOURED FILM

The present invention relates to a water permeable, apertured, contoured polymeric film in which the film is formed from an elastomer. The contoured, apertured film of the invention is suitable for use as a cover for absorbent devices such as sanitary napkins, incontinence pads and surgical dressings and therefore the present invention also relates to absorbent devices containing the contoured apertured film and to their manufacture.

It is desirable that body fluid such as blood, urine or wound exudate entering the absorbent material of an absorbent device such as a sanitary napkin, diaper, bed pad, incontinence pad, surgical dressing or bandage should be dispersed throughout the absorbent material in order to utilise its full absorptive capacity. It is an undesirable feature of current absorbent device design that absorbed fluid may re-emerge at the entry point or at sites distant from the entry point when localised pressure is brought to bear on the absorbent device. This phenomenon of the re-emergence of absorbed fluid is commonly termed 'wet-back'.

The two main methods by which it was sought to reduce wet-back were:

(a) to employ specially designed coverstock, that is the material which contacts or may contact the body of the wearer in use and (b) to employ a separator layer between the coverstock and absorbent.

These improved coverstocks and separator layers were formed essentially from hydrophobic water permeable films or non-woven fabrics which were often coated with surfactant to facilitate passage of the aqueous body fluid into the absorbent.

British Pat. No. 1526778 describes an absorbent structure in which the top sheet (that is the skin contacting sheet) is formed from a fluid impervious material provided with tapered capillaries in which each capillary has a single opening at the apex of the capillary for passage of liquid to the absorbent material. This patent does not disclose or suggest the use of elastomeric polymers to form the material of the top sheet.

European Patent Application No. 0171268 describes a non-adherent wound dressing which comprises an absorbent in a porous bag. The porous bag is formed from a contoured net of a thermoplastic elastomeric polymeric film. The film has a regular pattern of geometrically shaped depressions each of which has a single apical opening.

U.S. Pat. No. 3292619 describes an absorbent dressing comprising a pad of absorbent material and a wound contacting surface comprising a thermoplastic film which has depressed portions containing a plurality of openings in which the peripheral edges of the openings are adhered to the absorbent. This patent does not disclose that the film could be an elastomeric polymer.

It has now been found that by using as a coverstock a water permeable, apertured, contoured, polymeric film formed from elastomeric polymer and in which the ratio of apertures to raised areas of greater than one, an absorbent device may be manufactured which has good absorbent and wet-back properties. Contoured apertured films formed from elastomeric polymer and in which the ratio of apertures to raised areas is greater than one are new. Such films when used to form the body contacting surface of an absorbent device help to provide a soft feel to the device.

Accordingly the present invention provides a water permeable, contoured, polymeric film which comprises a film containing apertures and which has a pattern of raised areas therein and in which the film is formed from elastomeric polymer and in which the ratio of apertures to raised areas is greater than unity.

Within the scope of the present invention are films in which the raised areas may contain different numbers of apertures for example some raised areas may contain no apertures, some raised areas may contain one aperture and some apertures may contain more than one aperture but the ratio of the total number of apertures to the total number of raised areas will be greater than unity.

Suitably each raised area will contain at least one aperture and preferably the ratio of apertures to raised areas will be greater than 2.

Suitably the apertures may be distributed throughout the raised areas in a random manner. However, it is possible but less preferred that by judicious choice of the frequency of the apertures and the raised areas, a film in which the apertures are distributed in a regular manner through the raised areas can be achieved.

Suitably the ratio of apertures to raised areas will be from 2 to 8, more suitably from 3 to 6 and preferably will be between 4 and 5.

Elastomeric polymer is polymer which has a recoverable elastic strain of at least 20% and more suitably at least 25%, preferably at least 50% and most preferably at least 100%.

Suitable elastomeric polymers include polyether ester, polyurethanes, styrene-butadiene and styrene-isoprene block copolymers, polyisobutadiene, and blends of ethylene-vinyl acetate copolymers with polyolefins for example with polystyrene.

Polymeric materials which are suitable for preparing the contoured apertured film of the invention include thermoplastic elastomeric polymers or polymer blends. Favoured elastomeric polymer is a blend of an ethylene-vinyl acetate copolymer and an incompatible polymer such as a polyolefin and in particular a polystyrene. A particularly preferred elastomeric material is a blend of from 40 to 90 parts by weight ethylene-vinyl acetate copolymer and 60 to 10 parts by weight of polystyrene and more preferably 60 to 90 parts by weight of ethylene-vinyl acetate copolymer and 40 to 10 parts by weight of polystyrene, for example 60 parts ethylene-vinyl acetate copolymer and 40 parts high impact polystyrene, 90 parts ethylene-vinyl acetate copolymer and 10 parts high impact polystyrene. If necessary the polymeric material may include up to 10% of fillers or whitening agents such as titanium dioxide. Thus another preferred elastomeric material comprises 90 parts ethylene-vinyl acetate copolymer, 10 parts high impact polystyrene and 4% by weight of the polymers, of titanium dioxide.

Other elastomeric material which is suitable for preparing the contoured apertured film of the invention includes elastomeric polyether ester block copolymers such as Hytrel 4056 (Trade Mark).

Other suitable materials include polyether polyamide block copolymers such as those which are designated Pebax (Trade mark). A suitable copolymer is Pebax 2533 SN 00.

Suitably the apertured film may be provided with contours by pressing against a roller or a plate carrying a pattern of raised areas surrounded by troughs of flat areas. The raised areas which give rise to the contours on the apertured film may be of any shape but raised areas which are in the form of truncated square pyramids or hexagons are preferred. The pattern of raised areas impressed in the apertured film and the frequency of apertures may be arranged so that any raised area may contain none, one or more than one aperture, indeed some of the apertures may fall in the land areas between the raised areas in the film. This gives a random appearance to the distribution of the apertures amongst the raised areas of the film even though such a distribution may have arisen by impressing a regular pattern of raised areas on a regular pattern of apertures in the film. This is in direct contrast to the films known in the prior art in which one aperture is present at the apex of each depressed area. Aptly each raised area will contain at least one aperture. In an apt form the pattern of raised areas and the frequency of apertures may give rise to a substantially regular distribution of apertures amongst the raised areas in which there are 2 to 4 apertures in each raised area.

Suitably the raised areas impressed in the apertured film will number per unit area from 4 to 30 raised areas per sq. cm and more suitably will be 5 to 20 raised areas per sq. cm and preferably 6 to 12 raised areas per sq. cm for example 8, 9 or 10 per sq. cm.

Suitably the apertured film may contain from 8 to 120 apertures per sq. cm, more suitably will contain from 15 to 90 apertures per sq. cm and preferably from 30 to 60 apertures per sq. cm.

Suitably the contoured apertured film may have raised areas which have at least two apertures in the wall of each raised area, more suitably will have from 2 to 8 apertures per raised area and preferably 2 to 4 apertures per raised area.

Favourably the area of each aperture may be from 0.01 sq. mm. to 1 sq. mm. and more favourably 0.1 sq. mm. to 1 sq. mm. and preferably 0.25 to 0.75 sq. mm.

Suitably the open area of the apertured film may comprise from 5% to 50% of the area of the film and more suitably 10 to 40% of the area of the film.

The elastomeric polymer film used to form the contoured, apertured film of the invention is usually formed by conventional extrusion methods of the polymer or polymer blend. Suitably the thickness of the film when extruded is from 25 to 200 μm and more suitably is 30 to 150 μm thick and preferably from 35 to 100 μm thick. The thickness will depend to some extent on the properties of the film as regards strength and softness. The contoured apertured film when used in a sanitary protection device or a surgical dressing where it contacts the skin should be soft whilst at the same time being strong enough to be worn without tearing.

The contoured apertured film itself will have a thickness as measured from the level of the plane of the non-raised area of the film to the top of the raised area. Suitably this thickness is from 0.2 to 3mm and more suitably is 0.5 to 2mm and preferably is 0.5 to 1.5mm. The contoured apertured film when used in an absorbent device therefore provides separation of the absorbent from the wearer.

The contoured apertured films of the present invention are particularly suitable for use in absorbent devices. Absorbent devices when used herein include sanitary napkins, diapers, incontinence pads, and in a somewhat different area, surgical dressings. In these devices the contoured apertured film comprises at least a part of the surface which may at some time in use contact the skin of the wearer. The film normally provides a dry surface and when placed under pressure serves to restrict passage of absorbed fluid whereby the wearer's skin remains in a substantially dry condition. The raised areas are arranged to face away from the body of the wearer and towards the absorbent material.

In a second aspect therefore the present invention comprises an absorbent device comprising an absorbent material and a water permeable, contoured, apertured film formed from elastomeric polymer as herein before defined.

Suitably the absorbent device is in the form of a sanitary napkin or diaper in which at least the body facing surface of the device includes contoured apertured film of the invention. Suitably the whole of the body facing surface comprises a contoured apertured film. Most aptly the device is a sanitary napkin. The sanitary napkin may have the conventional structure which the skilled worker would recognise as usual in the art, that is a liquid pervious body facing layer, absorbent material and a fluid impermeable backing layer. The facing layer and fluid impermeable backing layer may be heat sealed around their edges to enclose the absorbent material.

Alternatively the contoured apertured film may extend around the whole of the absorbent material to overlap on the garment facing side and the edges adhered by for example a hot melt or pressure sensitive adhesive. In this embodiment a fluid impermeable layer may be placed at least between the garment facing side of the absorbent and apertured film. In yet a further alternative the contoured apertured film may form a strip in part of a larger piece of film whereby the contoured and apertured portion of the film forms the body contacting surface and the adjacent non-apertured and optionally non-contoured portions of the film are wrapped around the remainder of the absorbent material to provide the fluid impermeable wrapper.

The absorbent material used in the invention can be any of the absorbent layers used in conventional hygienic absorbent pads. Suitable absorbent materials for such layers include comminuted/fluffed wood pulp, carded cotton webs, viscose rayon fibres, tissue wadding, grafted cellulose super absorbents, polymeric super absorbents or mixtures thereof. The absorbent layer can optionally contain an insert such as a tissue wadding to aid fluid distribution within the layer.

In a further embodiment of this aspect of the invention the absorbent device may be in the form of a surgical dressing.

The contoured apertured film may be prepared as follows: a film is formed from elastomeric material by, for example, conventional blending and/or extrusion methods. The film may also contain fillers, whiteners, plasticisers, surfactants and the like to aid processing and to provide satisfactory surface characteristics and appearance to the finished film. The film may then be apertured using the normal methods used in the art including flame perforation and pin moulds with heated or non-heated pins. In one method the film may be placed against a pin mould and covered by a plain polyethylene film. The three layer sandwich is then compressed where upon the pins of the pin mould aperture the elastomer film removing a piece of that film having the area of the pin. These pieces of film adhere to the polyethylene film. On removal of the compressive force, the polyethylene film along with the small pieces of elastomeric film are then removed to reveal a substantially flat apertured film of the elastomeric polymer.

The apertured film may then be contoured by placing it on the surface of a thermoplastic film, such as a polypropylene film, which has discrete raised areas for example 10 raised areas per sq. cm. The raised areas may be coated with a silicone release agent to facilitate removal of the formed contoured apertured film. The raised areas may be of any shape but either square truncated pyramids or hexagonal shapes are preferred. The apertured film is contoured by compressing it against the raised areas of the film. Usually a resilient material, such as a foam, is present on the other side of the apertured film. The compression may be provided by a conventional press or by passing between the nip of a two rollers. It is possible that additional apertures may be placed in the already apertured film at this stage. These additional apertures are formed in the film at the tip of each of the raised areas in the thermoplastic film. The conditions of temperature and pressure used in the process will depend upon the properties of the elastomeric film employed. After this treatment the contoured apertured film may be peeled off the thermoplastic film. The size of the raised areas and the pattern of bosses employed will vary depending upon the size of apertures in the elastomeric film. The raised areas of the film may be adapted in size so that at least two apertures fall in the walls of each of the raised areas formed in the apertured film during the compression process.

Alternatively the apertured film may be contoured by passing it between two rollers one or both of which may have a pattern of raised and/or depressed areas on their surface. The rollers may be heated to a suitable temperature to assist in contouring the film. In one method only one roller carries a pattern of raised areas on its surface. The other roller, the smooth roller, preferably has a soft resilient surface of rubber or foam which allows the raised areas on the other roller, which is normally made of hard material such as metal, to press into and permanently deform the apertured film. A preferred method is to use two rollers which have an intermeshing pattern of raised and depressed areas on their surface.

In a further aspect therefore the present invention provides a process for the preparation of a water permeable, contoured film formed from elastomeric polymer which film contains apertures and has a pattern of raised areas therein, which process comprises forming apertures in a film of the elastomeric polymer and then compressing the apertured film against a pattern of raised and/or depressed areas whereby a pattern of raised areas is impressed in the apertured film, the number of apertures and raised areas being such that the ratio of apertures to raised areas is greater than unity.

EXAMPLE 1

A polymer blend containing 60 parts by weight of ethylene-vinyl acetate copolymer (containing 28% vinyl acetate) and 40 parts by weight of high impact polystyrene and 4% by weight of the polymer of titanium dioxide was formed by mixing the polymers in a blade mixer heated to 165° C. for 4 minutes. The resultant mix was removed from the mixer and formed into a sheet using a heated roll mill. This sheet was allowed to cool and then granulated in a Masson cutter.

A film was made from the polymer blend granules using a Brabender Extrusiograph extruder (length to diameter screw ratio of 25:1) driven by a Brabender PLE 651 Plasticorder and extruding the mixture through a 150mm film die into a nip of a two roller casting unit placed near the die. The resultant film had a thickness of 125 $\mu$m.

The film was taken and apertures formed in it by compression between a pin mould and a flat rigid film of polyethylene. On removal of the compressive force and the polyethylene film, a flat apertured film of the elastomeric polymer was obtained. The general configuration of the apertures was square having a side of approximately 0.5mm and hence an area of 0.25 sq. mm, the open area was 19%.

The apertured film was then placed on the embossed surface of a polypropylene sheet, which had a pattern of raised discrete, hexagonal bosses on that surface. A resilient polyurethane foam was placed over the apertured film. This sandwich was subjected to pressure and heat, 80° C. for 5 minutes. The polymer blend film had been formed into water permeable, contoured, apertured film material under the influence of the heat and pressure and could then be removed from the embossed surface of the plastics sheet.

An absorbent core (width 60 mm, length 216 mm) of comminuted fluff pulp (6.6 g), having a central layer insert of folded tissue wadding was placed centrally onto a strip of the apertured film (width 70 mm, length 240 mm) so that the openings in the film were in contact with the absorbent core. A film of liquid impervious film, polyethylene, was placed over the other side of the absorbent core and heat sealed around its edges to the apertured film is that the absorbent core is sandwiched between the two films.

A portion or portions of the outer facing surface of the liquid impervious film may carry a pressure sensitive adhesive layer covered by a release paper whereby in use the absorbent device in the form of a sanitary napkin may be adhered to a garment of the wearer.

EXAMPLE 2

Contoured apertured film was formed in a similar manner to that described in Example 1. Prior to preparing the sanitary napkin the embossed surface of the apertured film was spray coated with an acrylic emulsion adhesive at a weight per unit area of 5 gsm (approx) so that when the absorbent core was placed in contact with the apertured film it was adhered thereto. The absorption of fluid by the absorbent core was not impaired by the adhesive.

EXAMPLE 3

An apertured film was formed in a similar manner to that described in Example 1 except that instead of using a polymer blend to form the film, the film was formed from an elastomeric polyetherester, Hytrel 4056, and the film was 85 $\mu$m in thickness. After aperturing and contouring the film maybe used to form the body contacting surface of a sanitary napkin.

EXAMPLE 4

A polymer blend containing 40 parts by weight of ethylene-vinyl acetate copolymer (containing 18% vinyl acetate content), 40 parts by weight of low density polyethylene, 20 parts by weight of polystyrene, 3% by weight of the polymer of titanium dioxide and 1% by weight of a compatible surfactant was formed in a similar manner to that described in Example 1.

An apertured film was prepared from this polymer blend by extruding it between the nip of two rollers, one engraved with grooves in an annular direction and the other engraved with grooves in an axial direction, the extruded film was stretched at a ratio of 2:1 in the machine direction and perforated using a pin mould perforation method. The resultant flat apertured film had a mass weight per unit area of 40 gsm, contained 90-100 apertures per sq cm which were ellipsoidal in shape having an aperture area of 0.27 sq mm and the film had an open area of 23%.

The apertured film was impressed with raised areas by passing it between the nip of two rollers one of which was engraved with square pyramidal embossments and the second a plain roller covered with a resilient coating of paper.

A sanitary napkin was prepared in a similar manner to that described in Example 1 in which the contoured apertured film formed the body contacting surface of the napkin.

EXAMPLE 5

A water permeable, contoured apertured film was prepared in the manner described in Example 4.

An absorbent core (width 60 mm, length 216 mm) of comminuted fluff pulp (6.6 g), having a centrally placed layer insert of folded tissue wadding was placed centrally onto a strip of the apertured film (width 150 mm, length 240 mm) so that the openings in the film were in contact with one face of the absorbent core. A film of liquid impervious polyethylene was placed over the exposed face of the core so that the surface of the core and a portion of the longitudinal side edges of the core were covered by the polyethylene. The apertured film was then folded around the absorbent core so that the edges overlapped and the edges were then sealed together and to the polyethylene film by means of a pressure sensitive adhesive. The polyethylene film formed a fluid impermeable barrier layer between the absorbent layer and the apertured, contoured film. The ends of the folded films were heat sealed so that the absorbent core was completely enclosed.

EXAMPLE 6

A water permeable, contoured, apertured film was prepared in a manner similar to that described in Example 4 except that only a strip 60 mm in width on the contoured film comprises raised areas containing apertures, the remainder of the film is contoured but non apertured.

An absorbent core of the composition and dimension described above was placed over the 60 mm strip of apertured contoured film. The remainder of the contoured film was folded around the absorbent core so that the edges overlapped. The edges were then adhered to each other with a pressure-sensitive adhesive and the ends heatsealed together to enclose the absorbent core. In this sanitary napkin the unapertured contoured film formed a liquid impermeable barrier layer over the garment facing surface of the absorbent core.

EXAMPLE 7

A water permeable, contoured, apertured elastomeric film was prepared in a manner similar to that described in Example 4 except that only a strip 60 mm in width in the film was in the form of a contoured apertured film, the remainder of the film was plain, uncontoured, unapertured and water impermeable.

An absorbent core of the composition and dimensions described above was placed over the 60 mm strip of apertured, contoured film. The remainder of the film was folded around the absorbent core so that the edges overlapped and were sealed together using a pressure sensitive adhesive. The ends of the film were heat sealed together so that the absorbent core was totally enclosed. The contoured, apertured film formed the body contacting surface of the absorbent device and the remainder of the film provided a fluid impermeable barrier layer.

Fluid Wet-Back Test

Sanitary napkins prepared according to Example 1 were subjected to a fluid wet back test which was carried out in the following manner.

A 2 Kg flat weight (dimensions 10×5 cm) was placed on the napkin and allowed to remain in placed for 2 minutes and then removed. 5ml of 1% saline solution coloured with lissamine green dye was delivered onto the centre of the napkin by means of a syringe pump at a rate of 1 ml/min and at a height of 1 cm above the napkin surface formed by the contoured apertured film. A pre-weighed stack of filter papers (Whatman No. 1 filter papers) were then placed over the wetted area of the towel and a 2 Kg flat weight (dimensions 10×5 cm) placed on the filter papers. After 1 minute, the filter papers were removed and weighed. The wet back expressed as grams of fluid was then calculated from the difference in weight of the filter papers before and after compression against the absorbent device. The results are the average of tests in five samples.

| Sample | Wet Back |
| --- | --- |
| Example 2 | 0.03 g |
| Example 4 | 0.02 g |
| Commercial napkin | 0.98 g |

I claim:

1. A water permeable, contoured polymeric film which comprises a film containing apertures and which has a pattern of raised areas therein, in which the film is formed from elastomeric polymer and in which the ratio of apertures to raised areas is greater than unity.

2. A film according to claim 1 in which the apertures are described in a random manner throughout the raised areas.

3. A film as claimed in either of claims 1 or 2 in which each raised area contains at least one aperture.

4. A film according to claim 3 in which the ratio of apertures to rasied areas is greater than 2.

5. A film according to claim 4 in which the film contains from 4 to 30 raised areas per sq. cm and each raised area contains from 2 to 4 apertures.

6. A film according to claim 1 in which the film contains from 8 to 120 apertures per sq. cm and has an open area comprising from 5% to 50% of the area of the film.

7. A film according to claim 1 in which the area of each aperture is from 0.1 sq. mm to 1 sq. mm.

8. A film according to claim 1 in which the thickness of the contoured film is from 0.2 to 3 mm.

9. A film according to claim 1 in which the elastomeric polymer has a recoverable elastic strain of at least 25%.

10. A film according to claim 1 in which the elastomeric polymer is a blend of from 40 to 90 parts by weight of ethylene-vinyl acetate copolymer with 60 to 10 parts by weight of incompatible polymer.

11. An absorbent device for body fluids comprising absorbent material and a body facing surface wherein at least a portion of the body facing surface comprises a water permeable, contoured polymeric film which comprises a film containing apertures and which has a pattern of raised areas therein, in which the film is formed from elastomeric polymer and in which the ratio of apertures to raised areas is greater than unity.

12. An absorbent device according to claim 11 which is in the form of a sanitary napkin.

13. A process for the preparation of a water permeable, contoured film formed from elastomeric polymer which film contains apertures and has a pattern of raised areas therein, which process comprises forming apertures in a film of the elastomeric polymer and then compressing the apertured film against a pattern of raised and/or depressed areas whereby a pattern of raised areas is impressed in the apertured film, the number of apertures and raised areas being such that the ratio of apertures to raised areas is greater than unity.

14. A process according to claim 13 in which the apertures are formed using a pin mould.

15. A process according to claim 13 in which the film after being apertured is compressed between a roller which carries a pattern of raised areas on its surface and a smooth roller having a resilient surface.

16. A process according to claim 13 in which the film after being apertured is compressed between a pair of rollers which have an intermeshing pattern of raised and depressed areas on their surface.

17. An absorbent device according to claim 11 in which the whole of the body facing surface of the device comprises a contoured apertured film.

18. An absorbent device according to claim 11 in which the apertures are distributed in a random manner throughout the raised areas of the film.

19. An absorbent device according to claim 11 in which each raised area of the film contains at least one aperture.

20. An absorbent device according to claim 19 in which the ratio of apertures to raised areas in the film is greater than 2.

21. An absorbent device according to claim 20 in which the film contains from 4 to 30 raised areas per sq. cm and each raised area contains from 2 to 4 apertures.

22. An absorbent device according to claim 11 in which the film contains from 8 to 120 apertures per sq. cm and has an open area comprising from 5% to 50% of the area of the film.

23. An absorbent device according to claim 11 in which the area of each aperture is from 0.1 sq. mm to 1 sq. mm.

24. An absorbent device according to claim 11 in which the thickness of the contoured film is from 0.2 to 3 mm.

25. An absorbent device according to claim 11 in which the elastomeric polymer has a recoverable elastic strain of at least 25%.

26. An absorbent device according to claim 11 in which the elastomeric polymer is a blend of from 40 to 90 parts by weight of ethylene-vinyl acetate copolymer with 60 to 10 parts by weight of incompatible polymer.

27. An absorbent device for body fluids comprising absorbent material and a body facing surface wherein at least a portion of the body facing surface comprises a water permeable, contoured polymeric film which comprises a film containing apertures and which has a pattern of raised areas therein, in which the film is formed from elastomeric polymer and in which the ratio of apertures to raised areas is from 2 to 8.

28. An absorbent device according to claim 11 which is in the form of a diaper.

29. An absorbent device according to claim 11 which is in the form of a surgical dressing which comprises an absorbent and a surface which in use contacts the skin wherein the surface comprises a water permeable, contoured polymeric film which comprises a film containing apertures and which has a pattern of raised areas therein, in which the film is formed from elastomeric polymer and in which the ratio of apertures to raised areas is greater than unity.

* * * * *